(12) United States Patent
Johnston et al.

(10) Patent No.: US 8,946,196 B2
(45) Date of Patent: Feb. 3, 2015

(54) METHODS FOR SYNTHESIZING AND PURIFYING AMINOALKYL TETRACYCLINE COMPOUNDS

(71) Applicant: Paratek Pharmaceuticals, Inc., Boston, MA (US)

(72) Inventors: Sean M. Johnston, Doylestown, PA (US); Tadeusz Warchol, Northborough, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 14/041,593

(22) Filed: Sep. 30, 2013

(65) Prior Publication Data

US 2014/0031319 A1 Jan. 30, 2014

Related U.S. Application Data

(60) Continuation of application No. 12/608,227, filed on Oct. 29, 2009, now abandoned, which is a division of application No. 12/110,627, filed on Apr. 28, 2008.

(60) Provisional application No. 60/926,461, filed on Apr. 27, 2007.

(51) Int. Cl.
  *C07C 231/12* (2006.01)
  *C07C 231/24* (2006.01)

(52) U.S. Cl.
  CPC .............. *C07C 231/24* (2013.01); *C07C 231/12* (2013.01); *C07C 2103/46* (2013.01)
  USPC .......................................... 514/152; 552/203

(58) Field of Classification Search
  USPC .................. 514/152; 552/205, 203
  See application file for complete search history.

(56) References Cited

U.S. PATENT DOCUMENTS

| | | | |
|---|---|---|---|
| 2,980,584 A | 4/1961 | Hammer |
| 2,990,331 A | 6/1961 | Neumann et al. |
| 3,062,717 A | 11/1962 | Hammer |
| 3,165,531 A | 1/1965 | Nelson et al. |
| 3,304,227 A | 2/1967 | Loveless |
| 3,454,697 A | 7/1969 | Joyner et al. |
| 3,557,280 A | 1/1971 | Weber et al. |
| 3,674,859 A | 7/1972 | Beutel et al. |
| 3,957,980 A | 5/1976 | Noseworthy |
| 4,018,889 A | 4/1977 | Armstrong |
| 4,024,272 A | 5/1977 | Rogalski et al. |
| 4,126,680 A | 11/1978 | Armstrong |
| 4,666,897 A | 5/1987 | Golub et al. |
| 4,704,383 A | 11/1987 | McNamara et al. |
| 4,925,833 A | 5/1990 | McNamara et al. |
| 4,935,412 A | 6/1990 | McNamara et al. |
| 5,258,371 A | 11/1993 | Golub et al. |
| 5,308,839 A | 5/1994 | Golub et al. |
| 5,321,017 A | 6/1994 | Golub et al. |
| RE34,656 E | 7/1994 | Golub et al. |
| 5,459,135 A | 10/1995 | Golub et al. |
| 5,523,297 A | 6/1996 | Pruzanski et al. |
| 5,532,227 A | 7/1996 | Golub et al. |
| 5,668,122 A | 9/1997 | Fife et al. |
| 5,770,588 A | 6/1998 | McNamara et al. |
| 5,773,430 A | 6/1998 | Simon et al. |
| 5,789,395 A | 8/1998 | Amin et al. |
| 5,827,840 A | 10/1998 | Ramamurthy et al. |
| 5,834,449 A | 11/1998 | Thompson et al. |
| 5,834,450 A | 11/1998 | Su |
| 5,837,696 A | 11/1998 | Golub et al. |
| 5,843,925 A | 12/1998 | Backer et al. |
| 5,919,774 A | 7/1999 | Bach et al. |
| 5,919,775 A | 7/1999 | Amin et al. |
| 5,929,055 A | 7/1999 | Ryan et al. |
| 5,977,091 A | 11/1999 | Nieman et al. |
| 5,998,390 A | 12/1999 | Ramamurthy et al. |
| 6,015,804 A | 1/2000 | Golub et al. |
| 6,043,225 A | 3/2000 | Shor et al. |
| 6,043,231 A | 3/2000 | Pruzanski et al. |
| 6,100,248 A | 8/2000 | Golub et al. |
| 6,231,894 B1 | 5/2001 | Stamler et al. |
| 6,277,061 B1 | 8/2001 | Golub et al. |
| 6,617,318 B1 | 9/2003 | Nelson et al. |
| 6,683,068 B2 | 1/2004 | Nelson et al. |
| 6,818,635 B2 | 11/2004 | Nelson et al. |
| 7,067,681 B2 | 6/2006 | Nelson et al. |
| 7,326,696 B2 | 2/2008 | Nelson et al. |
| 7,553,828 B2 | 6/2009 | Nelson et al. |
| 7,595,309 B2 | 9/2009 | Nelson et al. |
| 7,696,186 B2 | 4/2010 | Nelson et al. |
| 7,696,187 B2 | 4/2010 | Nelson et al. |
| 2003/0125348 A1 | 7/2003 | Nelson et al. |
| 2004/0214801 A1 | 10/2004 | Nelson et al. |
| 2005/0026876 A1 | 2/2005 | Nelson et al. |
| 2005/0187198 A1 | 8/2005 | Nelson et al. |
| 2006/0287283 A1 | 12/2006 | Amoo et al. |
| 2008/0015169 A1 | 1/2008 | Nelson et al. |
| 2009/0156842 A1 | 6/2009 | Seyedi et al. |

(Continued)

FOREIGN PATENT DOCUMENTS

| | | |
|---|---|---|
| WO | WO-0119784 A1 | 3/2001 |
| WO | WO-0204406 A2 | 1/2002 |

(Continued)

OTHER PUBLICATIONS

Berge et al., "Pharmaceutical Salts", J. Pharm. Sci., 66:1-19 (1977).
Chandler et al., "Matrix metalloproteinases, tumor necrosis factor and multiple sclerosis: an overview", J. Neuroimmunol., 72: 155-161 (1997).

(Continued)

*Primary Examiner* — Sabiha N Qazi

(74) *Attorney, Agent, or Firm* — McCarter & English, LLP; Elizabeth A. Hanley

(57) ABSTRACT

Methods for the synthesis and purification of 9-amino alkyl tetracycline compounds are described.

28 Claims, No Drawings

(56) References Cited

U.S. PATENT DOCUMENTS

| | | | |
|---|---|---|---|
| 2009/0306022 A1 | 12/2009 | Nelson et al. | |
| 2009/0325908 A1 | 12/2009 | Nelson et al. | |
| 2010/0113400 A1* | 5/2010 | Nelson et al. | 514/152 |
| 2010/0160263 A1 | 6/2010 | Nelson et al. | |
| 2012/0283201 A1* | 11/2012 | Nelson et al. | 514/25 |
| 2013/0029943 A1 | 1/2013 | Nelson et al. | |

FOREIGN PATENT DOCUMENTS

| | | |
|---|---|---|
| WO | WO-0204407 A2 | 1/2002 |
| WO | WO-0272532 A1 | 9/2002 |
| WO | WO-0375857 A2 | 9/2003 |
| WO | WO-2004091513 A2 | 10/2004 |
| WO | WO-200909042 A1 | 1/2009 |

OTHER PUBLICATIONS

Dorwald, FA "Side Reactions in Organic Synthesis", Wiley: VCH, Weinheim, p. IX of Preface (2005).

Greenwald et al., "In Vitro Sensitivity of the Three Mammalian Collagenases to Tetracycline Inhibition: Relationship to Bone and Cartilage Degradation", Bone, 22(1):33-38 (1998).

Li et al., "Immunological Characterization of Cell-Surface and Soluble Forms of Membrane Type 1 Matrix Metalloproteinase in Human Breast Cancer Cells and in Fibroblasts", Mol. Carcinog., 22:84-89 (1998).

Liedtke et al., "Effective Treatment of Models of Multiple Sclerosis by Matrix Metalloproteinase Inhibitors", Ann. Neurol., 44:35-46 (1998).

Ryan et al., "Potential of tetracyclines to modify cartilage breakdown in osteoarthritis", Curr. Op. Rhuematol., 8:238-247 (1996).

Stetler-Stevenson et al., "Tumor Cell Interactions with the Extracellular Matrix During Invasion and Metastasis", Annu. Rev. Cell Biol., 9:541-573 (1993).

Tryggvason et al., "Proteolytic degradation of extracellular matrix in tumor invasion", Biochim. Biophys. Acta, 907:191-217 (1987).

Van den Bogert et al., "Doxycycline in Combination Chemotherapy of a Rat Leukemia", Cancer Res., 48:6686-6690 (1988).

Waitz, J.A., "Methods for Dilution Antimicrobial Susceptibility Tests for Bacteria that Grow Aerobically", Natl. Comm. Clin. Lab. Standards, Document M7-A2., 10(8):13-20 (1990).

* cited by examiner

METHODS FOR SYNTHESIZING AND PURIFYING AMINOALKYL TETRACYCLINE COMPOUNDS

Related Applications

This application is a continuation of U.S. patent application Ser. No. 12/608,227, filed on Oct. 29, 2009, which is a division of U.S. patent application Ser. No. 12/110,627, filed Apr. 28, 2008, which claims the benefit of U.S. Provisional Patent Application No. 60/926,461, filed Apr. 27, 2007. The entire contents of each of these applications are hereby incorporated herein by reference.

BACKGROUND OF THE INVENTION

The development of the tetracycline antibiotics was the direct result of a systematic screening of soil specimens collected from many parts of the world for evidence of microorganisms capable of producing bactericidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 25 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., *pneumococci* and *Salmonella*). The rise of tetracycline-resistant organisms has resulted in a general decline in use of tetracyclines and tetracycline analogue compositions as antibiotics of choice.

SUMMARY OF THE INVENTION

In one embodiment, the invention pertains, at least in part, to a method of synthesizing an aminoalkyl tetracycline compound. The method includes contacting a tetracycline compound with an N-hydroxymethyl-phthalimide in the presence of a water scavenger and an acid under appropriate conditions, such that an aminomethyl tetracycline intermediate compound is formed.

In another embodiment, the invention pertains, at least in part, to a method for the synthesis of an aminoalkyl tetracycline compound. The method includes: contacting a tetracycline compound with a N-hydroxymethyl-phthalimide in the presence of a water scavenger and an acid under appropriate conditions to form an aminomethyl tetracycline intermediate compound; treating the aminomethyl tetracycline intermediate compound with methylamine under second appropriate conditions to form a second aminomethyl tetracycline intermediate; and treating the second aminomethyl tetracycline intermediate under appropriate hydrogenation conditions, such that an aminomethyl tetracycline compound is formed.

In another embodiment, the invention pertains, at least in part, to a method of purifying alkylaminomethyl minocycline compounds by injecting an aqueous low pH solution of the compound into an HPLC in a polar organic solvent gradient, and combining the product fractions containing the alkylaminomethyl minocycline compound.

In yet another embodiment, the invention pertains, at least in part, to a method of removing hydrophobic impurities and oxidative degradents from an alkylaminomethyl minocycline compound. The invention includes dissolving the minocycline compound in an aqueous solution of a pH of 4.0-4.5, washing the aqueous solution with a non-polar organic solvent, and retaining the aqueous solution, such that hydrophobic impurities and oxidative degradents are removed from the alkylaminomethyl minocycline compound.

In yet another embodiment, the invention also pertains, at least in part, to a method of removing the β epimer and by products from an alkylaminomethyl minocycline compound. The method includes dissolving the minocycline compounds in an aqueous solution of a pH of 7.5-8.5, washing the aqueous solution with a non-polar organic solvent, and retaining the organic solution, such that the β epimer and by products are removed from the alkylaminomethyl minocycline compound.

In yet another embodiment, the invention includes pharmaceutical compositions comprising a tetracycline compound synthesized and/or purified by the methods of the invention and a pharmaceutically acceptable carrier.

In yet another embodiment, the invention includes a method for treating a tetracycline responsive state in a subject, by administering to the subject an effective amount of a tetracycline compound synthesized and/or purified by the methods of the invention.

DETAILED DESCRIPTION OF THE INVENTION

1. Methods for Synthesizing Amino-Methyl Tetracycline Compounds

In an embodiment, the invention pertains to an improved synthesis of 4-α-9-amino methyl tetracyclines with low 4-β-epimer content. Epimerization of tetracycline compounds at the C-4 position has been a challenge for chemists working to synthesize new tetracycline derivatives.

In one embodiment, method of synthesizing an aminoalkyl tetracycline compound, comprising contacting a tetracycline compound with a N-hydroxymethylphthalimide in the presence of an acid and a water scavenger under appropriate conditions, such that an aminomethyl tetracycline intermediate compound is formed.

The term "tetracycline compound" includes many compounds with a similar ring structure to tetracycline. Examples of tetracycline compounds include: tetracycline, chlortetracycline, oxytetracycline, demeclocycline, methacycline, sancycline, doxycycline, and minocycline. Other derivatives and analogues comprising a similar four ring structure are also included. Table I depicts tetracycline and several known tetracycline derivatives. The C-4 position is marked by an arrow.

TABLE I

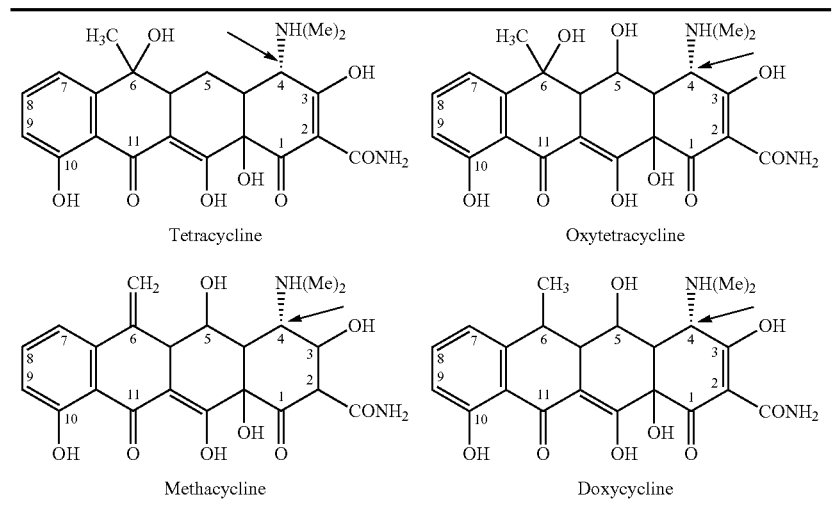

Tetracycline

Oxytetracycline

Methacycline

Doxycycline

The tetracycline compound may be substituted at any position of the tetracycline ring. For example, the tetracycline compound may further be substituted at the 1, 2, 3, 4, 5, 6, 7, 8, 10, 10a, 11, 11a, 12, 12a, and/or 13 position. The term tetracycline compound also includes compounds of the formula (I):

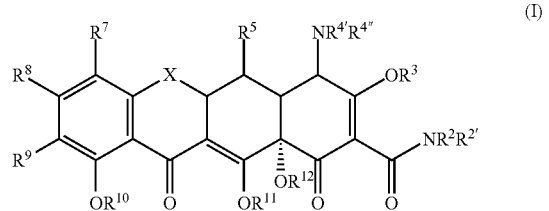

wherein

X is $CHC(R^{13}Y'Y)$, $CR^{6'}R^6$, S, $NR^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{11}$ and $R^{12}$ are each hydrogen, or a pro-drug moiety;

$R^{10}$ is hydrogen, a prodrug moiety, or linked to $R^9$ to form a ring;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, halogen, nitro, alkyl, alkenyl, heterocyclic, acyl, alkynyl, aryl, alkoxy, alkylthio, alkylsulfinyl, alkylsulfonyl, arylalkyl, amino, arylalkenyl, arylalkynyl, or —$(CH_2)_{0-3}(NR^{7c})_{0-1}C(=W')WR^{7a}$;

$R^9$ is hydrogen;

W is $CR^{7d}R^{7e}$, S, $N^{7b}$ or O;

W' is O, $NR^{7f}$S;

$R^{7a}$, $R^{7b}$, $R^{7c}$, $R^{7d}$, $R^{7e}$, and $R^{7f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

In a further embodiment, the tetracycline compound is minocycline. The structure of minocycline is shown below:

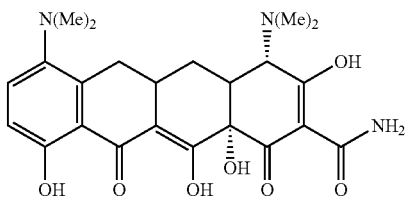

The term "N-hydroxymethyl phthalimide" includes compounds of the formula:

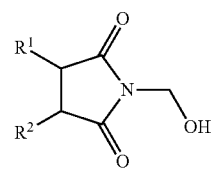

wherein

R$^1$ and R$^2$ are each hydrogen, alkyl, halogen, alkenyl, alkynyl, aryl, cyano, amino, amidino, alkoxy, and acyl. In a further embodiment, R$^1$ and R$^2$ are each alkyl or hydrogen.

The term "acid" includes organic acids such as triflic acid, methane sulfonic acid, and fuming sulfuric acid. Other acids known in the art are also included such as hydrochloric, sulfuric, phosphoric, hydrobromic, etc.

The term "water scavenger" includes agents which remove moisture from the reaction. These agents include acid chlorides and acid anhydrides (e.g., methyl sulfonic anhydride).

In certain embodiments, the reaction is conducted at a temperature of about 20-25° C. In certain embodiments, the reaction is stirred for about 1-2 hours after the addition of a first portion of N-hydroxymethylphthalimide. An additional portion of N-hydroxyphthalimide may be added, keeping the temperature between 20-35° C. The reaction may be continued until HPLC analysis of an aliquot of the reaction confirms that less than 4 area percent of mono-alkylated minocycline is remaining. The reaction conditions may further comprise a work up of adding the solution to an ice chilled flask of water, where the temperature is kept below 25° C. The product may be filtered, washed with water, and brought to a neutral pH. In a further embodiment, the appropriate conditions include an inert atmosphere (e.g., nitrogen or argon). In addition, the aminomethyl tetracycline intermediate may further be dissolved in acetone or acetonitrile to effect a more precise neutralization.

In another further embodiment, the resulting aminomethyl tetracycline intermediate comprises a 9:1 ratio of bis substituted (e.g., substituted at the 2 and 9 position) to tris substituted (e.g., substituted at the 2, 9 and 10 position). In a further embodiment, the amount of bis substituted amino methyl tetracycline compound is greater than about 50%, greater than about 60%, greater than about 70%, greater than about 80%, or greater than about 90%.

In a further embodiment, the aminomethyl tetracycline intermediate compound may be of the formula:

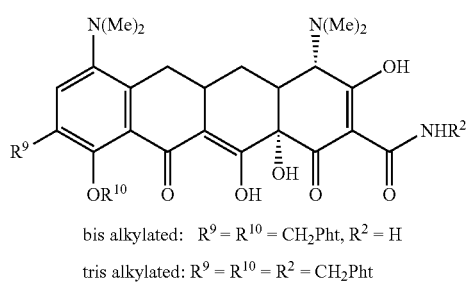

bis alkylated: R$^9$ = R$^{10}$ = CH$_2$Pht, R$^2$ = H tris alkylated: R$^9$ = R$^{10}$ = R$^2$ = CH$_2$Pht The aminomethyl tetracycline intermediate may be further treated with methylamine to form an aminomethyl tetracycline compound. The treatment with methylamine may be performed in an alkyl alcohol (e.g., EtOH, MeOH, etc.) solvent. The phthalamide by-product which forms may be removed by precipitation and the product may be precipitated from a mixture of cyclic/alkyl ether and alkyl alcohol in a ratio of about 1.5:1. In a further embodiment, the appropriate amount of the alkyl alcohol is an amount sufficient to prevent the precipitation of an aminomethyl tetracycline intermediate from the reaction.

In a further embodiment, the invention pertains to a method for the synthesis of an aminoalkyl tetracycline compound. The method includes contacting a tetracycline compound with a N-hydroxymethyl-phthalimide in the presence of an acid and a water scavenger under appropriate conditions to form an aminomethyl tetracycline intermediate compound; treating said aminomethyl tetracycline intermediate compound with methylamine under second appropriate conditions to form a second aminomethyl tetracycline intermediate; treating the second aminomethyl tetracycline intermediate under appropriate hydrogenation conditions, such that an amino methyltetracycline compound is formed. In a further embodiment, the tetracycline compound is minocycline.

In a further embodiment, the second appropriate conditions include dissolving the aminomethyl tetracycline intermediate compound in cyclic or alkyl ether and an appropriate amount of an alkyl alcohol. The alkyl alcohol may be used, for example, to selectively precipitate the by products and the cyclic or alkyl ether may be used to selectively precipitate the aminoalkyl tetracycline intermediate.

The resulting second aminomethyl tetracycline intermediate can then be isolated as a free base. Different salts of the free base can also be formed to effect a purification. Examples of acids which can be used to convert the free base to a salt include, but are not limited to, HCl, trifluoroacetic acid, methylsulfonic acid, and acetic acid. For example, when precipitating a hydrochloride salt, hydrochloric acid in isopropanol is added to a suspension of the compound in methanol to a pH of about 3.0. The mixture is stirred and filtered if necessary to remove insoluble constituents. The salt of the second aminomethyl tetracycline may be precipitated with t-butylmethylether and isolated by filtration. The salts of the second aminomethyl tetracycline intermediates may then directly undergo hydrogenation.

Examples of second aminomethyl tetracycline intermediates include compounds of the formula:

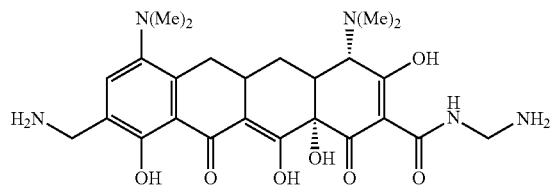

In a further embodiments, the appropriate hydrogenation conditions include transferring the second aminomethyl tetracycline intermediate to a hydrogenation flask and charging the flask with Pd/C or Pd/C/S either wet or as a dry powder. The reaction may be conducted using solvent such as methanol and an aldehyde. Appropriate hydrogenation conditions also include the use of hydrogen gas, which may be incorporated by conducting the reaction under a pressure of about 30 psi. The hydrogenation may occur for an appropriate length of time, such as about 24 hours. An example of an amino methyl tetracycline compound is:

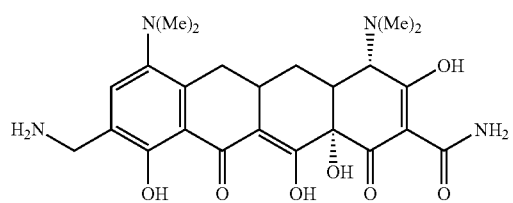

In a further embodiment, the aminomethyl tetracycline compound is contacted with an aldehyde or ketone under appropriate conditions, such that a substituted aminomethyl tetracycline compound is formed. Examples of substituted aminomethyl tetracycline compounds, include compounds of the formula:

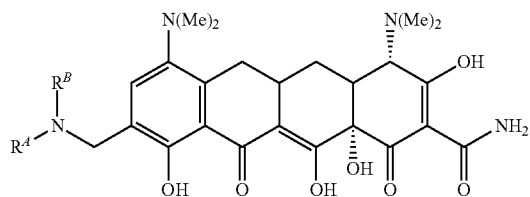

wherein $R^A$ and $R^B$ are each independently hydrogen, alkyl, alkenyl, alkynyl or aryl.

In one embodiment, $R^B$ is hydrogen and $R^A$ is alkyl (e.g., $(CH_3)_3CCH_2—$). In another embodiment, the substituted aminomethyl tetracycline compound is:

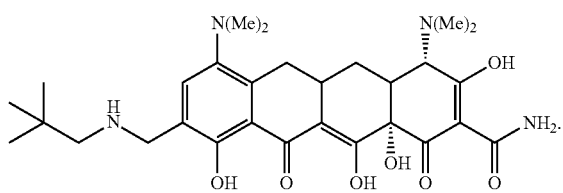

The 4-α and the 4-β epimer of an aminomethyl minocycline compound are shown below. The arrow marks the C-4 position of the tetracycline ring system,

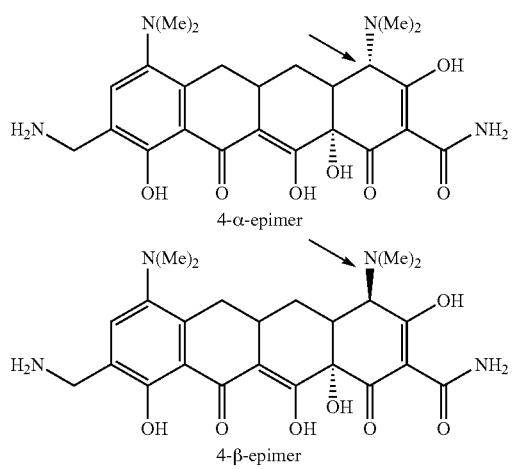

The term "epimeric purity" refers to the % of the tetracycline compounds (e.g., a tetracycline compound of the invention, (e.g., a substituted aminoalkyl tetracycline compound, an aminomethyl tetracycline compound, or an alkylaminomethyl minocycline compound) in a given sample with a particular desired epimeric configuration. In one embodiment, the epimeric purity of a tetracycline compound of the invention is greater than 95% of the α-epimer of a tetracycline compound at the C-4 position. In a further embodiment, the epimeric purity of the tetracycline compound is at least 96%, at least 97%, at least 98%, at least 99%, at least 99.5%, or at least 99.9% the α-epimer at the C-4 position of the tetracycline compound.

Preferably, the substituted aminoalkyl tetracycline compound, aminomethyl tetracycline compound, or alkylaminomethyl minocycline compound of the invention comprises mostly (e.g., at least 50%) α-C-4 epimer. In a further embodiment, the compound is about 60% α-C-4 epimer, about 70% α-C-4 epimer, about 80% α-C-4 epimer, about 90% α-C-4 epimer, at least about 95% α-C-4 epimer, or at least about 97% α-C-4 epimer. In a further embodiment, the substituted aminoalkyltetracycline compound, aminomethyl tetracycline compound, or alkylaminomethyl minocycline compound of the invention comprises less than about 7% β-C-4 epimer, less than about 5% β-C-4 epimer, or less than about 3% α-C-4 epimer.

The epimeric purity of a particular tetracycline compound made by the methods of the invention can be determined by using methods known in the art. For example, epimeric purity can be determined by HPLC or high field NMR.

In one embodiment, any hydrophobic impurities and oxidative degradents of the aminoalkyl tetracycline compound, aminomethyl tetracycline compound, or alkylaminomethyl minocycline compound of the invention (e.g., late-eluting hydrophobic impurities such as 4-carbonyl by products and other oxidative degradents from the acidic aqueous solution of particular compound of the invention) may be removed by washing the aqueous solution with a nor-polar organic solvent (e.g., $CH_2Cl_2$). The organic layers may be discarded and the aqueous layers may then be combined and retained.

2. Methods for the Isolation and Purification of 9-Alkyl Amino Methyl Tetracycline Compounds In another embodiment, the invention pertains to methods of purifying 9-alkyl amino methyl tetracyclines (or any tetracycline compound capable of being purified by the present methods) from impurities, β-epimer, and by products.

In one embodiment, the invention pertains to a method of purifying alkylaminomethyl minocycline compounds using chromatography. The method includes injecting an aqueous low pH solution of the compound into an HPLC in a polar organic solvent gradient, and combining the product fractions, such that the alkylaminomethyl minocycline compound is purified.

It has been found that selection of suitable acidic mobile phases enhances process stability and selectivity. Organic and mineral acid mobile phases may be effective for separating by-products including epimer impurities and closely-eluting by products through pH control or choice of acid. Acidic mobile phases may also protect against oxidative degradation of the minocycline compound.

In a further embodiment, the low pH solution has a pH of between about 2-3. Examples of solutions that may be used include 0.1% aqueous solutions of methane sulfonic acid. In certain embodiments, an isocratic gradient of 94% of the aqueous solution and 6% acetonitrile or another polar organic solvent may be used to purify the minocycline compound from epimeric and closely eluting by-products.

The resulting aqueous product fractions may be combined and the pH may be adjusted to between about 4.0-4.5 using a base (e.g., NaOH). Hydrophobic impurities and oxidative degradents of the minocycline compound may be removed by washing the aqueous solution with a non-polar organic solvent (e.g., $CH_2Cl_2$). The organic layers may then be discarded and the aqueous layers are combined and retained.

It should be noted that the organic solvents, such as methylene chloride, may be used to selectively remove late-eluting hydrophobic impurities such as 4-carbonyl by products and other oxidative degradents from the acidic aqueous solution of the minocycline compound.

The pH of the combined aqueous layers may then be adjusted to neutral pH, e.g., about 7.5 to about 8.5. The pH may be adjusted by the addition of a base, such as NaOH. The neutral solution is then washed with a non-polar organic solvent, such as methylene chloride. It should be noted that selective pH adjustment to neutral pH ranges also allows the minocycline compound to be extracted into the organic solvent while retaining undesired β-epimer and by products are dissolved the aqueous phase.

In addition, antioxidants may also be added to the aqueous solutions of minocycline compounds described herein. The antioxidants may be provided to prevent oxidative degradation of the minocycline compounds. Suitable antioxidants include, for example, sulfites (e.g., meta bisulfite, bisulfite, ammonium sulfite, etc.), citric acid, etc.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (e.g., isopropyl, tert-butyl, isobutyl, etc.), cycloalkyl (alicyclic) groups (e.g., cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 20 or fewer carbon atoms in its backbone (e.g., $C_1$-$C_{20}$ for straight chain, $C_3$-$C_{20}$ for branched chain), and more preferably 4 or fewer. Cycloalkyls may have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, triazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 20 or fewer carbon atoms in its backbone (e.g., $C_2$-$C_{20}$ for straight chain, $C_3$-$C_{20}$ for branched chain). Likewise, cycloalkenyl groups may have from 3-8 carbon atoms in their ring structure, and more preferably have 5 or 6 carbons in the ring structure. The term $C_2$-$C_{20}$ includes alkenyl groups containing 2 to 20 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butyryl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 20 or fewer carbon atoms in its backbone (e.g., $C_2$-$C_{20}$ for straight chain, $C_3$-$C_{20}$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including, e.g., alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkenyl, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "amide" or "aminocarboxy" includes compounds or moieties which contain a nitrogen atom which is bound to the carbon of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is hound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "aroyl" includes compounds and moieties with an aryl or heteroaromatic moiety bound to a carbonyl group. Examples of aroyl groups include phenylcarboxy, naphthyl carboxy, etc.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "halogen" includes fluorine, bromine, chlorine, iodine, etc. The term "perhalogenated" generally refers to a moiety wherein all hydrogens are replaced by halogen atoms.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O⁻X⁺, where X⁺ is a counter ion.

The terms "polycyclyl" or "polycyclic radical" refer to two or more cyclic rings (e.g., cycloalkyls, cycloalkynyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or hetero aromatic moiety.

The term "thiocarbonyl" or "thiocarboxy" includes compounds and moieties which contain a carbon connected with a double bond to a sulfur atom.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

3. Pharmaceutical Compositions Comprising Tetracycline Compounds of the Invention In a further embodiment, the invention pertains to pharmaceutical compositions comprising a tetracycline compound of the invention (e.g., synthesized, or purified by the methods of the invention) or a pharmaceutically acceptable salt, prodrug or ester thereof. The pharmaceutical compositions may comprise a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" is art recognized and includes relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Farm. SCI.* 66:1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances includes relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl and propyl esters. (See, for example, Berge et al., supra.).

The invention also pertains to tetracycline compounds, which are synthesized and/or purified by the methods of the invention, and pharmaceutically acceptable salts thereof.

4. Methods of Using the Tetracycline Compounds of the Invention

The invention also pertains to a method for treating a tetracycline responsive state in a subject, by administering to the subject an effective amount of a tetracycline compound synthesized and/or purified by the method the invention or a pharmaceutically acceptable salt thereof, such that the state is treated.

The term "treating" includes curing as well as ameliorating at least one symptom of the state, disease or disorder, e.g., the tetracycline compound responsive state.

The language "tetracycline compound responsive state" or "tetracycline responsive state" includes states which can be treated, prevented, or otherwise ameliorated by the administration of a tetracycline compound of the invention. Tetracycline compound responsive states include bacterial, viral, and fungal infections (including those which are resistant to other tetracycline compounds), cancer (e.g., prostate, breast, colon, lung melanoma and lymph cancers and other disorders characterized by unwanted cellular proliferation, including, but not limited to, those described in U.S. Pat. No. 6,100,248), arthritis, osteoporosis, diabetes, and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.,* 48:6686-6690 (1988)). In a further embodiment, the tetracycline responsive state is not a bacterial infection. In another embodiment, the tetracycline compounds of the invention are essentially non-antibacterial. For example, non-antibacterial tetracycline compounds of the invention may have MIC values greater than about 4 µg/ml (as measured by assays known in the art and/or the assay given in Example 2).

Tetracycline compound responsive states also include inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPAF's include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

Tetracycline compound responsive states also include NO associated states. The term "NO associated state" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Other examples of NO associated states include, but are not limited to, malaria, senescence, diabetes, vascular stroke, neurodegenerative disorders (Alzheimer's disease & Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

The term "inflammatory process associated state" also includes, in one embodiment, matrix metalloproteinase associated states (MMPAS). MMPAS include states characterized by aberrant amounts of MMPs or MMP activity. These are also include as tetracycline compound responsive states which may be treated using compounds of the invention.

Examples of matrix metalloproteinase associated states ("MMPAS's") include, but are not limited to, arteriosclerosis, corneal ulceration, emphysema, osteoarthritis, multiple sclerosis (Liedtke et al., *Ann. Neural.* 1998, 44:35-46; Chandler et al., *J. Neuroimmunol.* 1997, 72:155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., *Annu. Rev. Cell Biol.* 1993, 9:541-73; Tryggvason et al., *Biochim. Biophys. Acta* 1987, 907:191-217; Li et al., *Mol. Carcinog.* 1998, 22:84-89)), metastasis, acute lung injury, stroke, ischemia, diabetes, aortic or vascular aneurysms, skin tissue wounds, dry eye, bone and cartilage degradation (Greenwald et al., *Bone* 1998, 22:33-38; Ryan et al., *Curr. Op. Rheumatol.* 1996, 8; 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In another embodiment, the tetracycline compound responsive state is cancer. Examples of cancers which the tetracycline compounds of the invention may be useful to treat include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostatic carcinoma, lung cancer, and a variety of other cancers as well. The methods of the invention also cause the inhibition of cancer growth in adenocarcinomas, such as, for example, those of the prostate, breast, kidney, ovary, testes, and colon.

In an embodiment, the tetracycline responsive state of the invention is cancer. The invention pertains to a method for treating a subject suffering or at risk of suffering from cancer, by administering an effective amount of a substituted tetracycline compound, such that inhibition cancer cell growth occurs, i.e., cellular proliferation, invasiveness, metastasis, or tumor incidence is decreased, slowed, or stopped. The inhibition may result from inhibition of an inflammatory process, down-regulation of an inflammatory process, some other mechanism, or a combination of mechanisms. Alternatively, the tetracycline compounds may be useful for preventing cancer recurrence, for example, to treat residual cancer following surgical resection or radiation therapy. The tetracycline compounds useful according to the invention are especially advantageous as they are substantially non-toxic compared to other cancer treatments. In a further embodiment, the compounds of the invention are administered in combination with standard cancer therapy, such as, but not limited to, chemotherapy.

Examples of tetracycline responsive states also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amylotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity. Further neurological disorders include, for example, those listed in the American Psychiatric Association's Diagnostic and Statistical manual of Mental Disorders (DSM), the most current version of which is incorporated herein by reference in its entirety.

The language "in combination with" another therapeutic agent or treatment includes co-administration of the tetracycline compound, (e.g., inhibitor) and with the other therapeutic agent or treatment, administration of the tetracycline compound first, followed by the other therapeutic agent or treatment and administration of the other therapeutic agent or treatment first, followed by the tetracycline compound. The other therapeutic agent may be any agent which is known in the art to treat, prevent, or reduce the symptoms of an IPAS. Furthermore, the other therapeutic agent may be any agent of benefit to the patient when administered in combination with the administration of an tetracycline compound. In one embodiment, the cancers treated by methods of the invention include those described in U.S. Pat. Nos. 6,100,248; 5,843, 925; 5,837,696; or 5,668,122, incorporated herein by reference in their entirety.

In another embodiment, the tetracycline compound responsive state is diabetes, e.g., juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy. In a further embodiment, the IPAS includes disorders described in U.S. Pat. Nos. 5,929,055; and 5,532,227, incorporated herein by reference in their entirety.

In another embodiment, the tetracycline compound responsive state is a bone mass disorder. Bone mass disorders include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline compound responsive state is acute lung injury. Acute lung injuries include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The invention also pertains to a method for treating acute lung injury by administering a substituted tetracycline compound of the invention.

The tetracycline responsive states of the invention also include chronic lung disorders. The invention pertains to methods for treating chronic lung disorders by administering a tetracycline compound, such as those described herein. The method includes administering to a subject an effective amount of a substituted tetracycline compound such that the chronic lung disorder is treated. Examples of chronic lung disorders include, but are not limited, to asthma, cystic fibrosis, and emphysema. In a further embodiment, the tetracycline compounds of the invention used to treat acute and/or chronic lung disorders such as those described in U.S. Pat. Nos. 5,977,091; 6,043,231; 5,523,297; and 5,773,430, each of which is hereby incorporated herein by reference in its entirety.

In yet another embodiment, the tetracycline compound responsive state is ischemia, stroke, or ischemic stroke. The invention also pertains to a method for treating ischemia, stroke, or ischemic stroke by administering an effective amount of a substituted tetracycline compound of the invention. In a further embodiment, the tetracycline compounds of the invention are used to treat such disorders as described in U.S. Pat. Nos. 6,231,894; 5,773,430; 5,919,775 or 5,789,395, incorporated herein by reference.

In another embodiment, the tetracycline compound responsive state is a skin wound. The invention also pertains, at least in part, to a method for improving the healing response of the epithelialized tissue (e.g., skin, mucusae) to acute traumatic injury (e.g., cut, burn, scrape, etc.). The method may include using a tetracycline compound of the invention (which may or may not have antibacterial activity) to improve the capacity of the epithelialized tissue to heal acute wounds. The method may increase the rate of collagen accumulation of the healing tissue. The method may also decrease the proteolytic activity in the epthithelialized tissue by decreasing the collagenolytic and/or gellatinolytic activity of MMPs.

In a further embodiment, the tetracycline compound of the invention is administered to the surface of the skin (e.g., topically). In a further embodiment, the tetracycline compound of the invention used to treat a skin wound, and other such disorders as described in, for example, U.S. Pat. Nos. 5,827,840; 4,704,383; 4,935,412; 5,258,371; 5,308,8391 5,459,135; 5,532,227; and 6,015,804; each of which is incorporated herein by reference in its entirety.

In yet another embodiment, the tetracycline compound responsive state is an aortic or vascular aneurysm in vascular tissue of a subject (e.g., a subject having or at risk of having an aortic or vascular aneurysm, etc.). The tetracycline compound may by effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the in vitro standard broth dilution method described in Waltz, J. A., *National Commission for Clinical Laboratory Standards, Document M7-A2*, vol. 10, no. 8, pp. 13-20, $2^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

The invention is further illustrated by the following examples, which should not be construed as further limiting.

EXEMPLIFICATION OF THE INVENTION

Example 1

Synthesis of 9-Alkyl Aminomethyl Minocycline

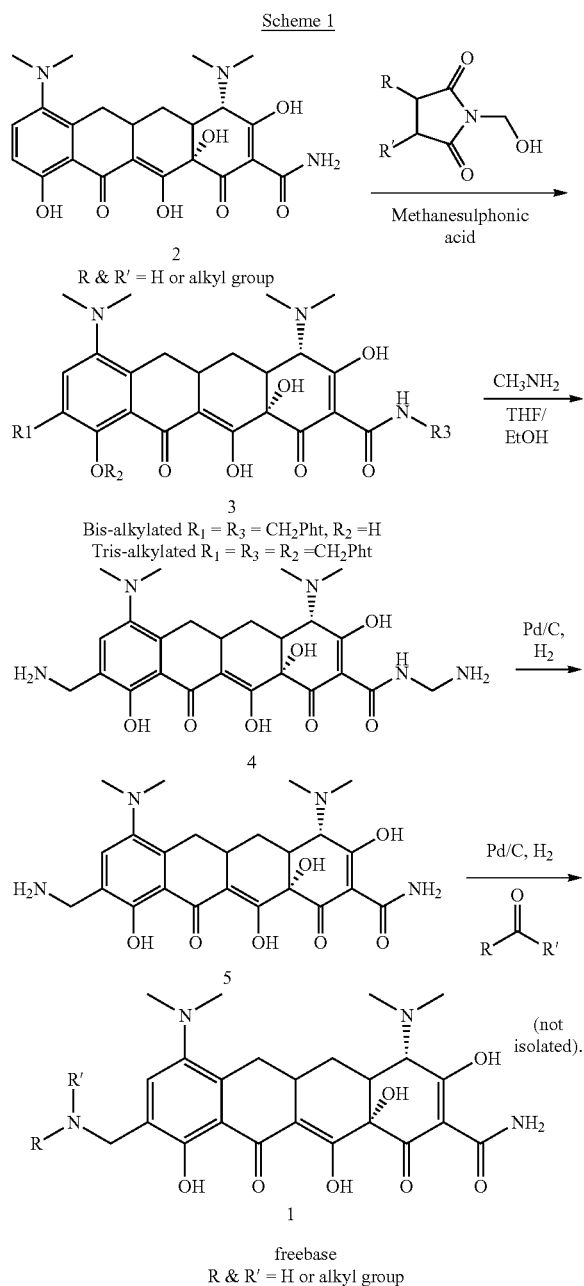

Minocycline hydrochloride (compound 2) was dissolved in methylsulfonic acid or hydrofluoric acid with methylsulfonic anhydride. N-hydroxymethyl phthalimide was added to the reaction mixture. The mixture was stirred at 20-35 C until the reaction was complete. The acid solution was added to an ice/water mixture and the triflic salt was readily precipitated, filtered and collected. The salt was re-dissolved in acetone and brought to a neutral pH with base. The product was precipitated by the addition of water. The product was isolated as a mixture of the bis and tris alkylated product. The isolated material of this reaction was enriched in the desired bis ratio (90%).

The solid was suspended in the EtOH. Aminolysis was carried out by using methylamine. A phthalamide by-product precipitated as the reaction progressed and was removed by filtration. The light yellow solid product was precipitated out by the addition of about 1.5 volumes of t-butylmethylether to the reaction mixture, and collected through a simple filtration that left many small impurities and methylamine reagent in the solution. Further purification of the compound was performed through re-slurrying with methanol.

Compound 4 as freebase was transferred to a hydrogenation vessel which was charged with methanol and aldehyde. An inactivated Pd/C catalyst was charged and the vessel was pressurized with hydrogen gas. The reaction mixture was hydrogenated under hydrogen pressure around 30 Psi for about 24 hours. When conversion of compound 4 to 1 was complete, the solution was filtered and washed through a Celite pad. At this point the reaction mixture contained very low β C-4 epimer, around 3-7%.

The product (1) was worked up and isolated selectively from its impurities. The pH of the solution was adjusted to about 4.5 with concentrated HCl and the solution was washed with dichloromethane. Sulfites were added to the aqueous layer and the product was extracted with dichloromethane at pH of about 7 to 8 to selectively recover the preferred epimer product (e.g., α). The dichloromethane layers were combined and concentrated, and 2 L of n-heptane was added to precipitate the product. Further purification was obtained by repeating the work-up procedure with or without t-butylmethylether to dissolve the crude product.

Example 2

Isolation and Purification of an 9-Alkyl Aminomethyl Minocycline Compound

Crude 9-(2',2'-dimethylpropyl aminomethyl)minocycline freebase (40 g) was dissolved in 150 mL of buffer A (0.1% aqueous solution of methanesulfonic acid—MSA) and the pH was adjusted to 2-3 with MSA.

The solution was filtered and injected into an HPLC and the product was eluted with an isocratic gradient of 94% buffer A and 6% acetonitrile. The product fraction collection was initiated when the product peak was detected. Each fraction was analyzed and an acceptance criterion of greater than 80% AUC of the main peak was used for the early product fractions. When combining fractions, the level of impurities and relative concentration of the pooled fractions was factored into the selection criteria that meets the final product specifications. To the product fractions was added a 10% aqueous solution of sodium sulfite equal to 10% of the original volume of the collected fractions.

A product fraction volume of 3.5 liters (including sodium sulfite) was collected and the pH was adjusted to 4.0-4.5 using a solution of sodium hydroxide. The aqueous solution was washed with 2 liters of dichloromethane and the organic layer was separated and discarded.

The pH of the aqueous layer was adjusted to 7.5-8.5 using sodium hydroxide and the product was extracted four times with 2.4 liters of dichloromethane. The pH was readjusted to 7.5 to 8.5 with sodium hydroxide, prior to each extraction.

The four dichloromethane layers were combined and concentrated to about 200 ml, which was then added slowly (over a period of about 10 minutes) to a vigorously stirred n-heptane (2.5 L). The suspension was stirred for about 10 minutes at room temperature and diluted slowly (over a period of 5 minutes) with n-heptane 1.5 L. The slurry was cooled to 0-5° C. and stirred for 1-2 hours. The suspended solid was filtered and washed with 3×150 mL portions of n-heptane. The product was dried under vacuum at 40° C. for at least 24 hours until a constant weight was achieved and the levels of all residual solvents were within specification. Approximately 13.6 g of 9-(2',2'-dimethylpropyl aminomethyl)minocycline freebase was isolated as a yellow solid.

The off-cuts were isolated in a similar manner and yielded 1.64 g.

Equivalents

Those skilled in the art will recognize, or be able to ascertain using no more than routine experimentation, many equivalents to the specific embodiments and methods described herein. Such equivalents are intended to be encompassed by the scope of the following claims.

All patents, patent applications, and literature references cited herein are hereby expressly incorporated by reference.

The invention claimed is:

1. A method of purifying an alkylaminomethyl minocycline compound, comprising:
   a) injecting a low pH aqueous solution of said alkylaminomethyl minocycline compound into a liquid chromatography device in a polar organic solvent gradient, and combining the product fractions;
   b) adjusting the pH of said product fractions to 4.0-4.5;
   c) washing said product fractions with a first non-polar organic solvent to form a first organic layer and a first aqueous layer, and discarding said first organic layer;
   d) adjusting the pH of said first aqueous layer to 7.5-8.5; and
   e) washing said first aqueous layer with a second non-polar organic solvent to form a second organic layer and a second aqueous layer, and discarding said second aqueous layer,
   such that said alkylaminomethyl minocycline compound is purified.

2. The method of claim 1, wherein said low pH aqueous solution has a pH of 2-3.

3. The method of claim 1, wherein said low pH aqueous solution comprises methyl sulfonic acid.

4. The method of claim 1, wherein said polar organic solvent is acetonitrile.

5. The method of claim 1, wherein said pH in step b) or d) is adjusted with a base.

6. The method of claim 5, wherein said base is selected from the group consisting of metal hydroxide, metal carbonate, metal bicarbonate, ammonia, organic primary amine, organic secondary amine and organic tertiary amine.

7. The method of claim 6, wherein said metal is selected from the group consisting of lithium, sodium, potassium, calcium, magnesium and aluminum.

8. The method of claim 6, wherein said base is sodium hydroxide or ammonia.

9. The method of claim 1, wherein said first non-polar organic solvent is methylene chloride.

10. The method of claim 1, wherein said first organic layer comprises by-products, hydrophobic impurities and oxidative degradents of said alkylaminomethyl minocycline compound.

11. The method of claim 1, wherein said second non-polar organic solvent is methylene chloride.

12. The method of claim 1, wherein said second aqueous layer comprises by-products and β epimer of said alkylaminomethyl minocycline compound.

13. The method of claim 1, wherein an antioxidant is added.

14. The method of claim 13, wherein said antioxidant is ammonium sulfite, sodium sulfite, bisulfite or meta bisulfite.

15. The method of claim 1, wherein said alkylaminomethyl minocycline compound is:

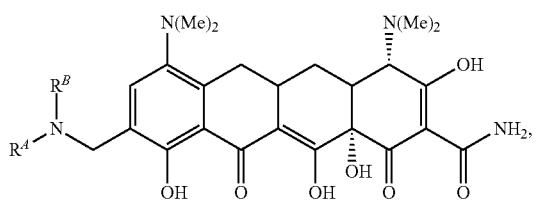

wherein $R^A$ is alkyl, and $R^B$ is hydrogen or alkyl.

16. The method of claim 15, wherein $R^B$ is hydrogen.

17. The method of claim 16, wherein $R^A$ is alkyl.

18. The method of claim 17, wherein said alkyl is $(CH_3)_3CCH_2-$.

19. The method of claim 1, wherein said alkylaminomethyl minocycline compound is:

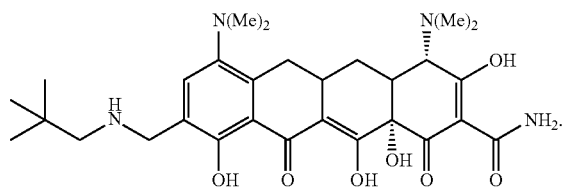

20. The method of claim 1, wherein hydrophobic impurities and oxidative degradents are removed from said alkylaminomethyl minocycline compound.

21. The method of claim 1, wherein by-products and β-C-4 epimer are removed from said alkylaminomethyl minocycline compound.

22. The method of claim 1, wherein said alkylaminomethyl minocycline compound is essentially free of hydrophobic impurities and oxidative degradents.

23. The method of claim 1, wherein said alkylaminomethyl minocycline compound is essentially free of by-products, β-C-4 epimer, hydrophobic impurities and oxidative degradents.

24. The method of claim 1, wherein said alkylaminomethyl minocycline compound comprises at least 50% α-C-4 epimer.

25. The method of claim 24, wherein said alkylaminomethyl minocycline compound comprises at least 95% α-C-4 epimer.

26. The method of claim 25, wherein said alkylaminomethyl minocycline compound comprises at least 99.9% α-C-4 epimer.

27. The method of claim 1, wherein said alkylaminomethyl minocycline compound comprises less than 7% β-C-4 epimer.

28. The method of claim 27, wherein said alkylaminomethyl minocycline compound comprises less than 3% β-C-4 epimer.

* * * * *